(12) United States Patent
Angibaud et al.

(10) Patent No.: US 6,177,432 B1
(45) Date of Patent: Jan. 23, 2001

(54) FARNESYLTRANSFERASE INHIBITING QUINAZOLINONES

(75) Inventors: Patrick René Angibaud, Fontaine-Bellenger; Marc Gaston Venet, Le Mesnil Esnard, both of (FR); Eddy Jean Edgard Freyne, Rumst (BE)

(73) Assignee: Janssen-Cilag S.A. (FR)

( * ) Notice: Under 35 U.S.C. 154(b), the term of this patent shall be extended for 0 days.

(21) Appl. No.: 09/403,705

(22) PCT Filed: Apr. 17, 1998

(86) PCT No.: PCT/EP98/02357

§ 371 Date: Oct. 22, 1999

§ 102(e) Date: Oct. 22, 1999

(87) PCT Pub. No.: WO98/49157

PCT Pub. Date: Nov. 5, 1998

(30) Foreign Application Priority Data

Apr. 25, 1997 (EP) .................................................. 97201259

(51) Int. Cl.[7] ........................ A61K 31/505; C07D 239/72
(52) U.S. Cl. ........................... 514/259; 514/274; 544/286; 544/283
(58) Field of Search ................................. 514/259, 274; 544/286, 283

(56) References Cited

FOREIGN PATENT DOCUMENTS

| 0 371 564 | 6/1990 | (EP) . |
| 664 128 * | 7/1995 | (EP) . |
| WO 96 15118 | 5/1996 | (WO) . |

* cited by examiner

*Primary Examiner*—Mukund J. Shah
*Assistant Examiner*—Sudhaker B. Patel
(74) *Attorney, Agent, or Firm*—Myra McCormack

(57) ABSTRACT

This invention concerns compounds of formula

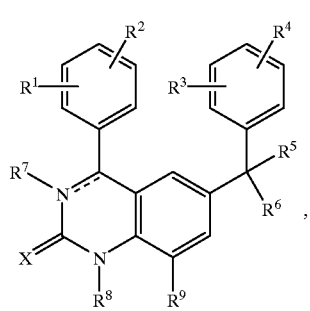

(I)

the pharmaceutically acceptable acid addition salts and the stereochemically isomeric forms thereof, wherein the dotted line represents an optional bond; X is oxygen or sulfur; $R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$lkyloxy, mono- or di($C_{1-6}$alkyl)amino$C_{1-6}$alkyloxy, $Ar^1$, $Ar^1C_{1-6}$alkyl, $Ar^1$oxy, $Ar^1C_{1-6}$alkyloxy; or when on adjacent positions $R^1$ and $R^2$ taken together may form a bivalent radical; $R^3$ and $R^4$ each independently are hydrogen, halo, cyano, $C_{1-6}$alkyl, $C_{1-6}$alkyloxy, $Ar^1$oxy, $C_{1-6}$alkylthio, di($C_{1-6}$alkyl)amino, trihalomethyl, trihalomethoxy; $R^5$ is hydrogen, halo, cyano, optionally substituted $C_{1-6}$alkyl, $C_{1-6}$alkyloxycarbonyl or $Ar^1$; or a radical of formula $-OR^{10}$, $-SR^{10}$, $-NR^{11}R^{12}$; $R^6$ is an optionally substituted imidazolyl moiety; $R^7$ is hydrogen or $C_{1-6}$alkyl provided that the dotted line does not represent a bond; $R^8$ is hydrogen, $C_{1-6}$alkyl or $Ar^2CH_2$ or $Het^1CH_2$; $R^9$ is hydrogen, $C_{1-6}$alkyl, $C_{1-6}$alkyloxy or halo, or $R^8$ and $R^9$ taken together may form a bivalent radical; $Ar^1$ and $Ar^2$ are optionally substituted phenyl and $Het^1$ is optionally substituted pyridinyl; having farnesyl transferase inhibiting activity; their preparation, compositions containing them and their use as a medicine.

12 Claims, No Drawings

FARNESYLTRANSFERASE INHIBITING QUINAZOLINONES

CROSS-REFERENCE TO RELATED APPLICATIONS

This application is the National Stage of PCT application PCT/EP98/02357, filed Apr. 17, 1998 which claims priority from EP Patent Application No. 97.201.259.5, filed Apr. 25, 1997.

The present invention is concerned with novel quinazolinone derivatives, the preparation thereof, pharmaceutical compositions comprising said novel compounds and the use of these compounds as a medicine as well as methods of treatment by administering said compounds.

Genetic research has led to the identification of a variety of gene families in which mutations can lead to the development of a wide variety of tumors. A particular group of genes, known as ras, have been identified in mammals, birds, insects, mollusks, plants, fungi and yeasts. The family of mammalian ras genes consists of three major members ("isoforms"): H-ras, K-ras and N-ras genes. These ras genes code for highly related proteins generically known as p21$^{ras}$. These p21$^{ras}$ proteins comprise a family of proteins that regulate cell growth when bound to the inner surface of the plasma membrane. However, overproduction of p21$^{ras}$ proteins, or mutations of said ras genes thereby coding for mutant or oncogenic forms of p21$^{ras}$ proteins, lead to uncontrolled cell division. In order to regulate cell growth, the ras proteins need to be attached to the inner leaflet of the plasma membranes. If mutated or oncogenic forms of p21$^{ras}$, the p21$^{ras}$ oncoproteins, become attached to plasma membranes, they provide a signal for the transformation of normal cells to tumor cells and promote their uncontrolled growth. To acquire this transforming potential, the precursor of the p21$^{ras}$ oncoprotein must undergo an enzymatically catalyzed farnesylation of the cysteine residue located in a carboxyl-terminal tetrapeptide. Therefore, inhibitors of the enzyme that catalyzes this modification, farnesyl protein transferase, will prevent the membrane attachment of p21$^{ras}$ and block the aberrant growth of ras-transformed tumors. Hence, it is generally accepted in the art that farnesyl transferase inhibitors can be very useful as anticancer agents for tumors in which ras contributes to transformation.

Since mutated or oncogenic forms of ras are frequently found in many human cancers, most notably in more than 50% of colon and pancreatic carcinomas (Kohl et al., Science, vol 260, 1834–1837, 1993), it has been suggested that farnesyl transferase inhibitors can be very useful against these types of cancer.

EP-0,371,564 discloses (1H-azol-1-ylmethyl) substituted quinoline, quinazoline and quinoxaline derivatives which suppress the plasma elimination of retinoc acids. Some of these compounds also have the ability to inhibit the formation of androgens from progestines and/or inhibit the action of the aromatase enzyme complex.

It has been found that the present novel compounds, all having a phenyl substituent on the 4-position of the 2-quinazolinone-moiety bearing a carbon or nitrogen-linked imidazolyl moiety, show farnesyl protein transferase inhibiting activity.

The present invention concerns compounds of formula

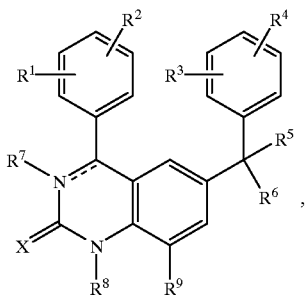

(I)

the pharmaceutically acceptable acid addition salts and the stereochemically isomeric forms thereof, wherein
the dotted line represents an optional bond;
X is oxygen or sulfur;
$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$ alkyloxy, mono- or di($C_{1-6}$alkyl)amino$C_{1-6}$alkyloxy, Ar$^1$, Ar$^1C_{1-6}$alkyl, Ar$^1$oxy, Ar$^1C_{1-6}$alkyloxy,
$R^3$ and $R^4$ each independently are hydrogen, halo, cyano, $C_{1-6}$alkyl, $C_{1-6}$alkyloxy, Ar$^1$oxy, $C_{1-6}$alkylthio, di($C_{1-6}$alkyl)amino, trihalomethyl or trihalomethoxy;
$R^5$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, mono- or di($C_{1-6}$alkyl)amino$C_{1-6}$alkyl, Ar$^1$, Ar$^1C_{1-6}$alkyloxy$C_{1-6}$alkyl; or a radical of formula —O—R$^{10}$, (a-1)

—S—R$^{10}$, (a-2)

—N—R$^{11}$R$^{12}$, (a-3)

wherein
$R^{10}$ is hydrogen, $C_{1-6}$alkyl, $C_{1-6}$alkylcarbonyl, Ar$^1$, Ar$^1C_{1-6}$alkyl, $C_{1-6}$alkyloxycarbonyl$C_{1-6}$alkyl, or a radical for formula —Alk—OR$^{13}$ or —Alk—NR$^{14}$R$^{15}$;
$R^{11}$ is hydrogen, $C_{1-6}$alkyl, Ar$^1$ or Ar$^1C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, Ar$^1$, Ar$^1C_{1-6}$alkyl, $C_{1-6}$alkylcarbonyl-$C_{1-6}$alkyl, Ar$^1$carbonyl, Ar$^1C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—OR$^{13}$ or —Alk—NR$^{14}$R$^{15}$;
wherein
Alk is $C_{1-6}$alkanediyl;
$R^{13}$ is hydrogen, $C_{1-6}$alkyl, $C_{1-6}$alkylcarbonyl, hydroxy$C_{1-6}$alkyl, Ar$^1$ or Ar$^1C_{1-6}$alkyl;
$R^{14}$ is hydrogen, $C_{1-6}$alkyl, Ar$^1$ or Ar$^1C_{1-6}$alkyl;
$R^{15}$ is hydrogen, $C_{1-6}$alkyl, $C_{1-6}$alkylcarbonyl, Ar$^1$ or Ar$^1C_{1-6}$alkyl;

$R^6$ is a radical of formula

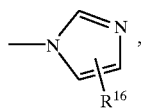
(b-1)

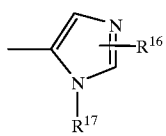
(b-2)

wherein $R^{16}$ is hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2$$C_{1-6}$alkyl;

$R^{17}$ is hydrogen, $C_{1-6}$alkyl or di($C_{1-4}$alkyl)aminosulfonyl;

$R^7$ is hydrogen or $C_{1-6}$alkyl provided that the dotted line does not represent a bond;

$R^8$ is hydrogen, $C_{1-6}$alkyl or $Ar^2CH_2$ or $Het^1CH_2$;

$R^9$ is hydrogen, $C_{1-6}$alkyl, $C_{1-6}$alkyloxy or halo; or $R^8$ and $R^9$ taken together to form a bivalent radical of formula

(c-1)

(c-2)

(c-3)

(c-4)

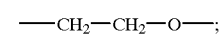
(c-5)

$Ar^1$ is phenyl; or phenyl substituted with 1 or 2 substituents each independently selected from halo, $C_{1-6}$alkyl, $C_{1-6}$alkyloxy or trifluoromethyl;

$Ar^2$ is phenyl; or phenyl substituted with 1 or 2 substituents each independently selected from halo, $C_{1-6}$alkyl, $C_{1-6}$alkyloxy or trifluoromethyl; and $Het^1$ is pyridinyl; pyridinyl substituted with 1 or 2 substituents each independently selected from halo, $C_{1-6}$alkyl, $C_{1-6}$alkyloxy or trifluoromethyl.

As used in the foregoing definitions and hereinafter, halo is generic to fluoro, chloro, bromo and iodo; $C_{1-2}$alkyl defines methyl or ethyl; $C_{1-4}$alkyl includes $C_{1-2}$alkyl and the higher homologues thereof having 3 to 4 carbon atoms such as, e.g. propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methylbutyl, hexyl, 2-methylpentyl and the like; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "S(O)" refers to a sulfoxide and "S(O)$_2$" to a sulfon.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid acid addition salts by treating said base form with an appropriate acid. Appropriate acids comprise, for example, inorganic acids such as hydrohalic acids, e.g. hydrochloric or hydrobromic acid; surfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

In those compounds where the dotted line does not represent a bond, the nitrogen on the 3-position of the quinazolinone moiety allows for an extra bond, i.e. radical $R^7$. In those compounds where the dotted line represents a bond, said radical $R^7$ is absent.

Wherever $R^8$ and $R^9$ are taken together to form a bivalent radical of formula (c-4) or (c-5), the $CH_2$ moiety in said bivalent radical is preferably connected to the nitrogen atom of the 2-quinazolinone moiety of the compounds of formula (I).

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:

a) $R^1$ and $R^2$ are each independently selected from hydrogen, halo, $C_{1-6}$alkyl, $C_{1-6}$alkyloxy or trihalomethyl; in particular hydrogen, halo or $C_{1-4}$alkyl;

b) $R^3$ and $R^4$ are each independently selected from hydrogen, halo, $C_{1-6}$alkyl, $C_{1-6}$alkyloxy or trihalomethyl; in particular hydrogen, halo or $C_{1-4}$alkyl;

c) $R^5$ is is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$ alkyl, or a radical of formula —$NR^{11}R^{12}$ wherein $R^{11}$ is hydrogen or $C_{1-6}$alkyl and $R^{12}$ is hydrogen, $C_{1-6}$alkyl, $C_{1-6}$alkyloxy, $C_{1-6}$alkyloxy$C_{1-6}$ alkylcarbonyl; in particular $R^5$ is hydrogen, hydroxy, halo, or amino;
d) $R^6$ is a radical for formula (b-1) or (b-2) wherein $R^{16}$ is hydrogen or $C_{1-6}$alkyl and $R^{17}$ is $C_{1-6}$alkyl;
e) $R^7$ is hydrogen or $C_{1-6}$alkyl in case the dotted line does not represent a bond;
f) $R^8$ is hydrogen, $C_{1-6}$alkyl or Het$^1$CH$_2$;
g) $R^9$ is hydrogen.

A particular group of compounds consists of those compounds of formula (I) wherein X is oxygen, $R^1$ and $R^2$ are each independently selected from hydrogen, halo, $C_{1-4}$alkyl; $R^3$ and $R^4$ are each independently selected from hydrogen, halo, $C_{1-4}$alkyl; $R^5$ is hydrogen, hydroxy, halo or a amino; $R^6$ is a radical of formula (b-1) or (b-2) wherein $R^{16}$ is hydrogen or $C_{1-4}$alkyl and $R^{17}$ is $C_{1-4}$alkyl; $R^7$ is hydrogen or $C_{1-4}$alkyl in case the dotted line does not represent a bond; $R^8$ is hydrogen; $C_{1-4}$alkyl or Het$^1$CH$_2$; and $R^9$ is hydrogen.

Preferred compounds are those compounds of formula (I) wherein X is oxygen, $R^1$ is 3-chloro, $R^2$ is hydrogen, $R^3$ is 4-chloro, $R^4$ is hydrogen, $R^5$ is hydrogen, $C_{1-2}$alkyl, halo or amino; $R^6$ is a radical of formula (b-1) or (b-2) wherein $R^{16}$ is hydrogen and $R^{17}$ is $C_{1-2}$alkyl; and $R^7$ is hydrogen or $C_{1-2}$alkyl in case the dotted line does not represent a bond; $R^8$ is hydrogen, $C_{1-2}$alkyl or Het$^1$CH$_2$; and $R^9$ is hydrogen.

The most preferred compounds of formula (I) are 6-[amino(4-chlorophenyl)(1-methyl-1H-imidazol-5-yl) methyl]-4-(3-chlorophenyl)-1-methyl-2(1H)-quinazolinone; and
6-[amino(4-chlorophenyl)(1-methyl-1H-imidazol-5-yl) methyl]-4-(3-chlorophenyl)-3,4-dihydro-1,3-dimethyl-2 (1H)-quinazolinone; the stereoisomeric forms and the pharmaceutically acceptable acid addition salts thereof.

The compounds of formula (I) wherein $R^6$ is a radical of formula (b-1), represented by compounds of formula (I-a), can generally be prepared by N-alkylating an intermediate of formula (III), with an intermediate of formula (II), wherein W is an appropriate leaving group such as, for example, chloro, bromo, methanesulfonyloxy or benzenesulfonyloxy. The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

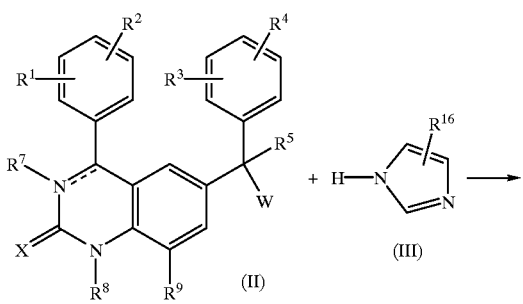

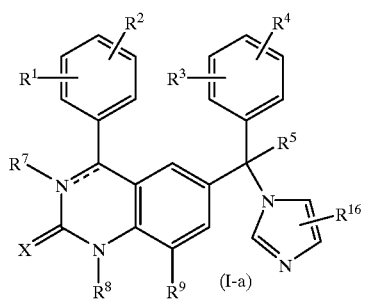

Also, compounds of formula (I-a) can be prepared by reacting an intermediate of formula (IV) with an intermediate of formula (V), wherein Y is carbon or sulfur, such as, for example, a 1,1'-carbonyldiimidazole.

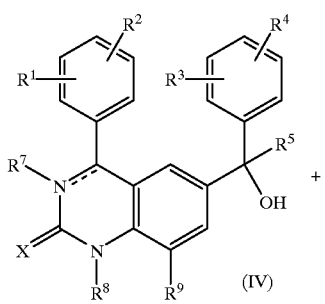

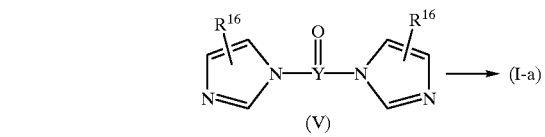

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

The compounds of formula (I) wherein $R^6$ represents a radical of formula (b-2), $R^5$ is hydroxy and $R^{17}$ is $C_{1-6}$alkyl, said compounds being referred to as compounds of formula (I-b-1) may be prepared by reacting an intermediate ketone of formula (VI) with an intermediate of formula (III-1). Said reaction requires the presence of a suitable strong base, such as, for example, butyl lithium in an appropriate solvent, such as, for example, tetrahydrofuran, and the presence of an appropriate silanederivative, such as, for example, triethylchlorosilane. During the work-up procedure an intermediate silane derivative is hydrolyzed. Other procedures with protective groups analogous to silanederivatives can also be applied.

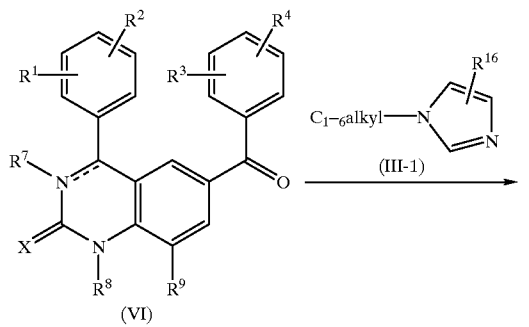

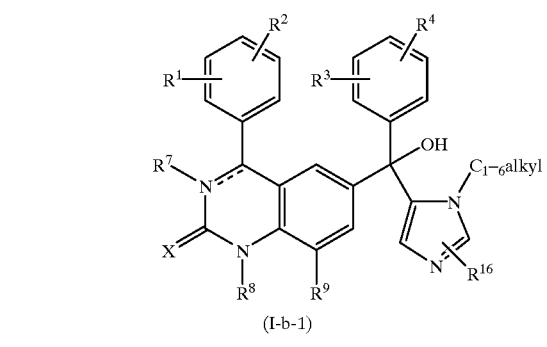

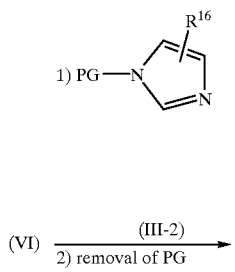

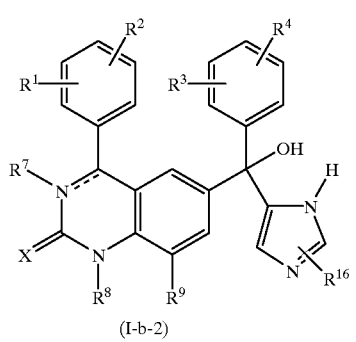

Also, the compounds of formula (I), wherein $R^6$ is a radical of formula (b-2), $R^5$ is hydroxy and $R^{17}$ is hydrogen, said compounds being referred to as compounds of formula (I-b-2) may be prepared by reacting an intermediate ketone of formula (VI) with an intermediate of formula (III-2), wherein PG is a protective group such as, for example, a sulfonyl group, e.g. a dimethylamino sulfonyl group, which can be removed after the addition reaction. Said reaction is conducted analogously as for the preparation of compounds of formula (I-b-1), followed by removal of the protecting group PG, yielding compounds of formula (I-b-2).

Compounds of formula (I-c), defined as compounds of formula (I) wherein $R^7$ is hydrogen and the dotted line does not represent a bond, can be converted into compounds of formula (I-d), defined as compounds of formula (I) wherein the dotted line represents a bond, by art-known oxidation procedures such as, e.g. oxidation with $MnO_2$ in a reaction-inert solvent, e.g. dichloromethane.

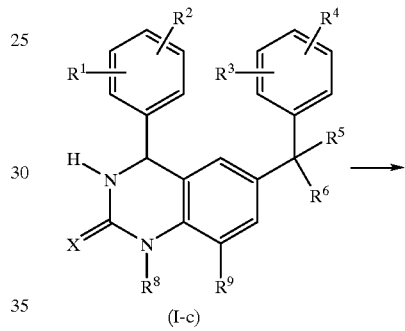

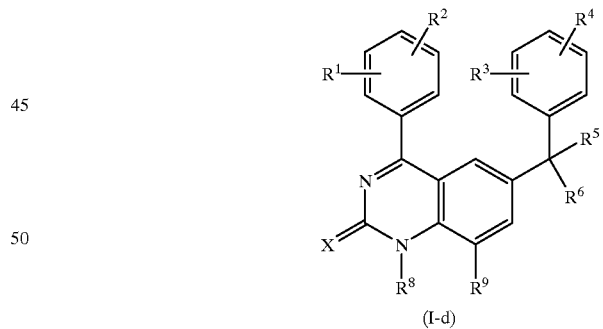

Conversely, compounds of formula (I-d) can be converted to compounds of formula (I-c) using art-known reduction procedures such as, e.g. treatment with sodiumborohydride in a suitable solvent, e.g. methanol.

Also, compounds of formula (I-c) can be converted to compounds of formula (I-c-1) by treating compounds (I-c) with a reagent of formula $R^7$-$W^1$, wherein $W^1$ is an appropriate leaving group such as, for example, chloro, bromo, methanesulfonyloxy or benzenesulfonyloxy, using the above-described N-alkylation procedure.

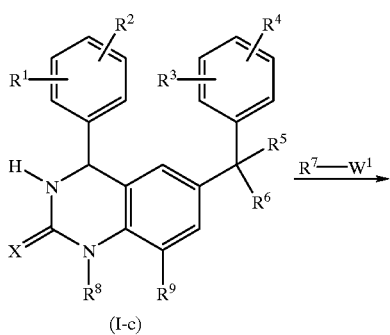

(I-c)

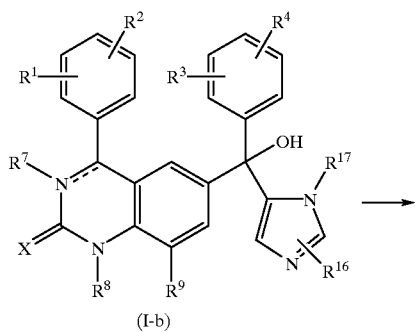

(I-c-1)

The compounds of formula (I-b) can be converted to compounds of formula (I-e), defined as a compound of formula (I) wherein $R^6$ is a radical of formula (b-2) and $R^5$ is hydrogen, by submitting the compounds of formula (I-b) to appropriate reducing conditions, such as, e.g. stirring in acetic acid in the presence of formamide.

(I-b)

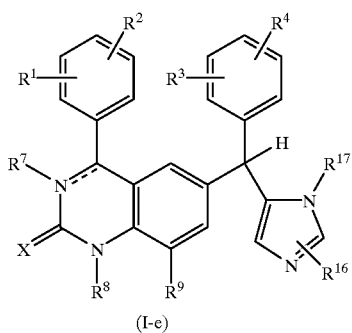

(I-e)

Further, compounds of formula (I-b) can be converted to compounds of formula (I-f) wherein $R^5$ is halo, be reacting the compounds of formula (I-b) with a suitable halogenating agent, such as, e.g. thionyl chloride or phosphorus tribromide. Successively, the compounds of formula (I-f) can be treated with a reagent of formula $H-NR^{11}R^{12}$ in a reaction-inert solvent, thereby yielding compounds of formula (I-g).

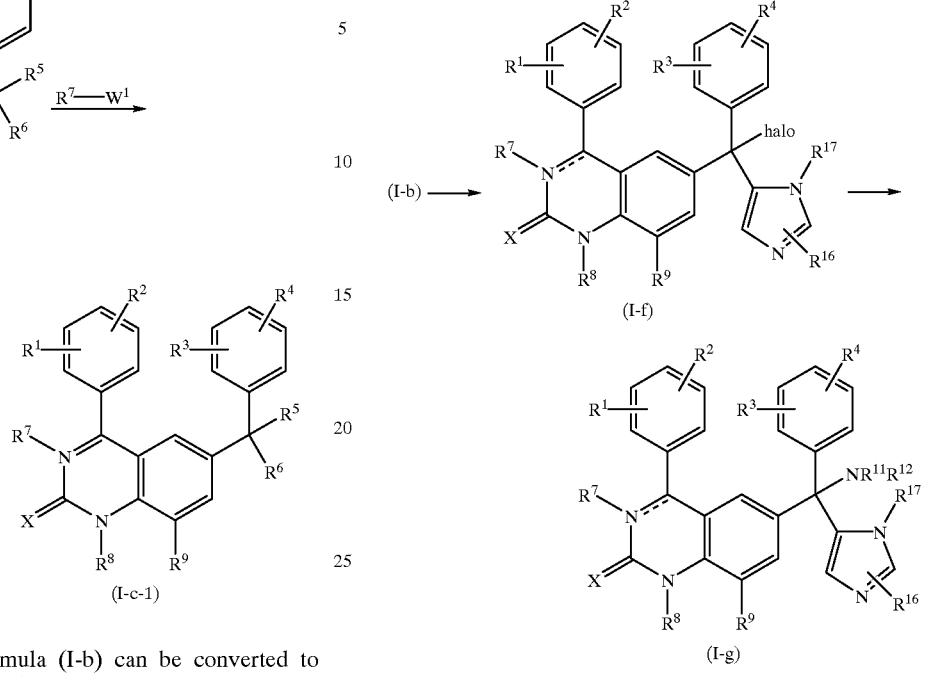

A compound of formula (I-i), defined as a compound of formula (I) wherein X is sulfur, may be prepared by reacting the corresponding compound of formula (I-h), defined as a compound of formula (I) wherein X is oxygen, with a reagent like phosphorus pentasulfide or Lawesson's reagent in a suitable solvent such as, for example, pyridine.

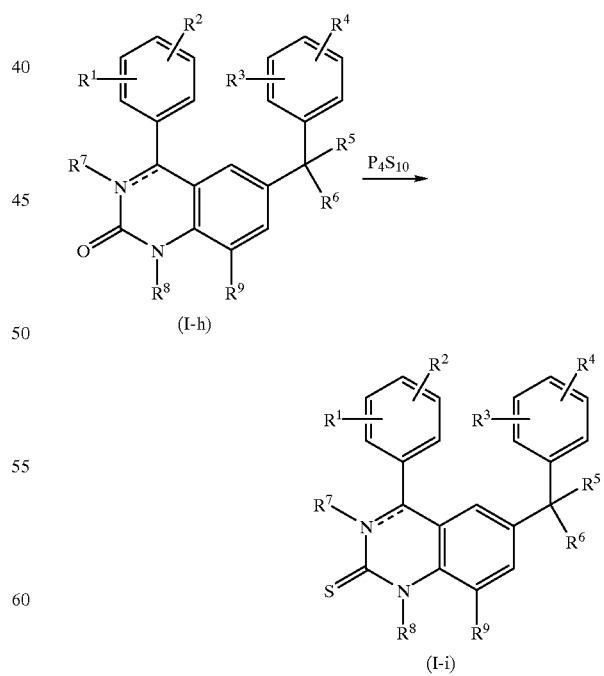

An intermediate of formula (II-a), being an intermediate of formula (II) wherein X is oxygen and $R^7$ and $R^8$ are hydrogen, can be prepared starting from an intermediate of formula (VII). Said intermediate (VII), wherein n is 2 or 3, is conveniently prepared by protecting the corresponding art-known ketone as a ketal. An intermediate of formula (VII) is reacted with an intermediate of formula (VIII) in the presence of a base such as sodium hydroxide, in an appropriate solvent, e.g. methanol. The thus obtained intermediate of formula (IX) undergoes ring opening of the isoxazole moiety by hydrogenation of intermediate (IX) in the presence of a suitable catalyst such as, e.g. Raney Nickel. Subsequent acylation with a reactive carboxylic acid derivative, e.g. trichloroacetyl chloride or trifluoroacetyl chloride, yields an intermediate of formula (X), which undergoes ring closure in the presence of an ammonium salt, e.g. ammonium acetate, and an appropriate base such as, e.g. hexamethylphosphorous triamide (HMPT). Intermediates of formula (X) are submitted to acidic conditions and subsequently treated with art-known reducing agents such as, e.g. sodium borohydride, yielding intermediates of formula (XII). The hydroxy group of intermediates of formula (XII) is converted to a leaving group W by treating intermediates (XII) with a suitable reagent such as, e.g. methanesulfonyloxy chloride, or a halogenating reagent such as, e.g. POCl$_3$ or SOCl$_2$, yielding intermediates of formula (II-a).

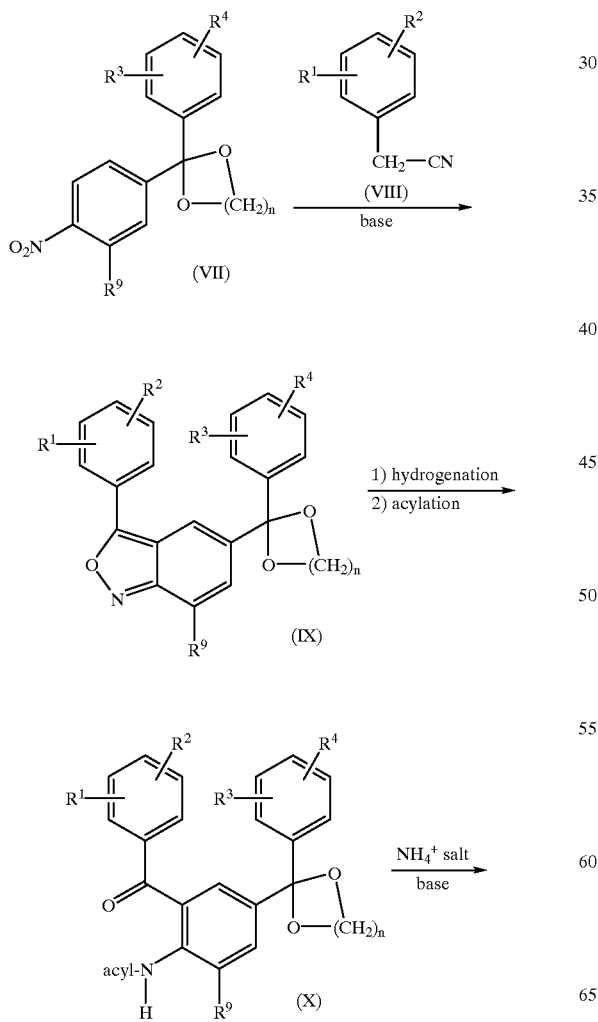

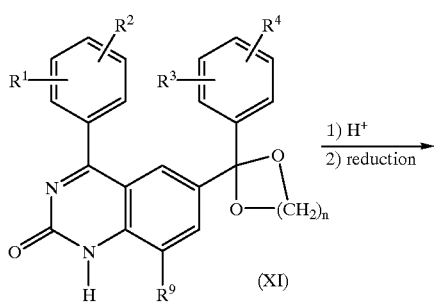

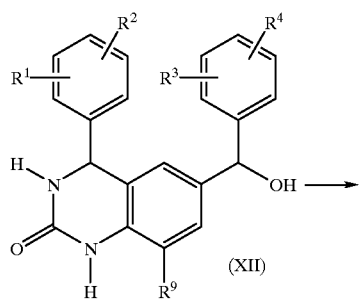

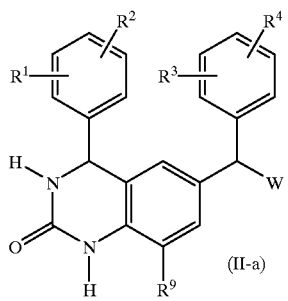

Intermediates for formula (II-b), defined as intermediates of formula (II) wherein X is O and R$^7$ is hydrogen, can be prepared by reacting intermediates of formula (XI) with R$^8$-W$^1$, wherein W$^1$ is a suitable leaving group such as, e.g. chloro, bromo, methanesulfonyloxy or benzenesulfonyloxy; using the above-described N-alkylation procedure. Subsequent reduction with e.g. sodiumborohydride in a suitable solvent, e.g. methanol, and hydrolysis under acidic conditions, yields intermediates of formula (XIV). Conversion of the hydroxy group of intermediates (XIV) into leaving group W, e.g. by treatment with methanesulfonyloxy chloride or a halogenating reagent such as, e.g. SOCl$_2$, POCl$_3$, gives intermediates of formula (II-b).

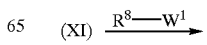

-continued

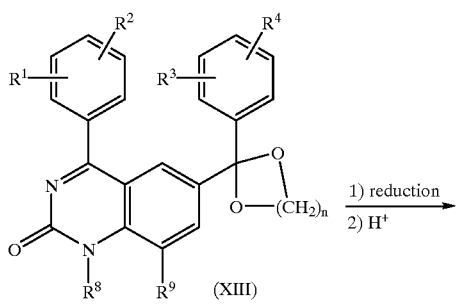

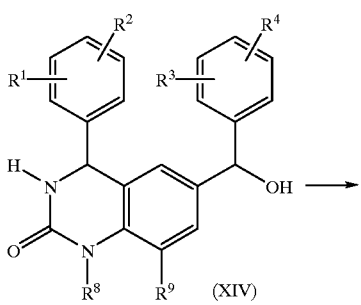

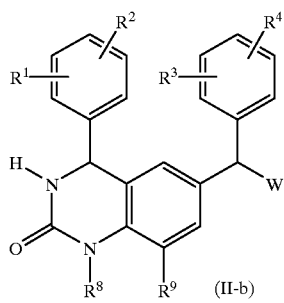

Intermediates of formula (VI-a), defined as intermediates of formula (VI) wherein X is O and the dotted line does not represent a bond, can be prepared by submitting intermediates of formula (XIII) to art-known reduction procedures, such as, e.g. treatment with sodium borohydride in a reaction-inert solvent e.g. methanol, thereby yielding intermediates of formula (XV). Intermediates (XV) are N-alkylated with $R^7$-$W^1$, wherein $W^1$ is a leaving group as above-described, and subsequently hydrolysed under acidic conditions to intermediates of formula (VI-a).

(XIII) ⟶

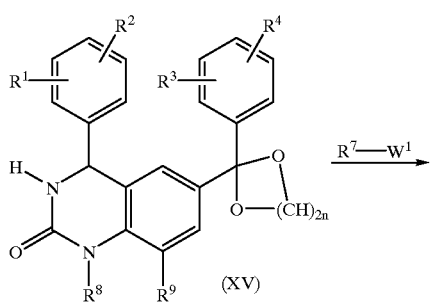

-continued

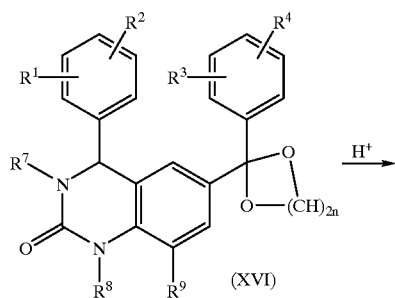

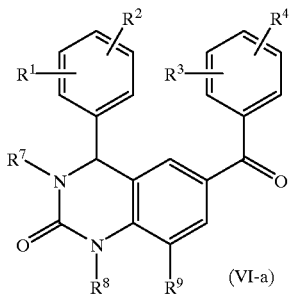

Also, intermediates of formula (VI-b), defined as intermediates of formula (VI) wherein X is O and the dotted line represents a bond, can be prepared by hydrolysis of the intermediate of formula (IX) with an acid, such as for example, TiCl$_3$, in the presence of water. Subsequent acylation with a reactive carboxylic acid derivative, such as, e.g. trichloroacetyl chloride, yields an intermediate of formula (XVII), which undergoes ring closure in the presence of an ammonium salt, e.g. ammonium acetate, and an appropriate base such as, e.g. hexamethylphosphorous triamide (HMPT), thereby yielding an intermediate of formula (VI-b).

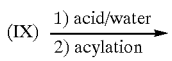

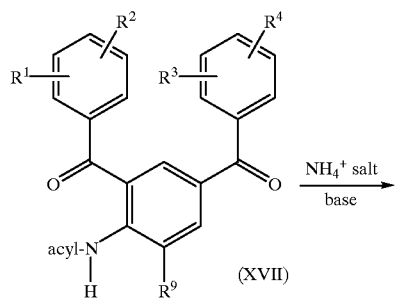

-continued

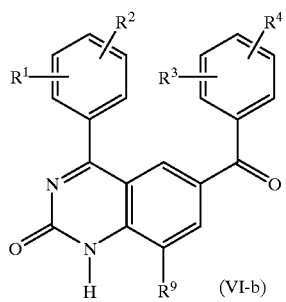

(VI-b)

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Specific stereoisomers can be synthesized by stereospecific methods of preparation. These methods will advantageously employ enantiomerically pure starting materials.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targetting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes, i.e. the ras gene itself is not activated by mutation to an oncogenic form, with said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes may be inhibited by the compounds of this invention.

Hence, the present invention discloses the compounds of formula (I) for use as a medicine as well as the use of these compounds of formula (I) for the manufacture of a medicament for treating one or more of the above mentioned conditions.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The following examples are provided for purposes of illustration.

EXPERIMENTAL PART

A. Preparation of the Intermediates

Hereinafter "THF" means tetrahydrofuran, "DIPE" means diisopropylether, "DCM" means dichloromethane, "DMF" means N,N-dimethylformamide and "ACN" means acetonitrile.

Of some compounds of formula (I) the absolute stereochemical configuration was not experimentally determined. In those cases the stereochemically isomeric form which was first isolated is designated as "A" and the second as "B", without further reference to the actual stereochemical configuration.

Example A.1 a) A mixture of (4-chlorophenyl)(4-nitrophenyl)methanone (0.0382 mol), 1,2-ethanediol (0.0764 mol) and 4-methylbenzenesulfonic acid monohydrate 96% (0.19 mol) in methylbenzene (150 ml) was stirred and refluxed in a Dean Stark apparatus for 24 hours. The mixture was washed with $K_2CO_3$ (10%) and then with water. The organic layer was dried, filtered off and evaporated. The product was used without further purification, yielding 11.42 g (98%) of 2-(4-chlorophenyl)-2-(4-nitrophenyl)-1,3-dioxolane (interm. 1).

b) Sodium hydroxide (0.818 mol) and then 3-chlorobenzeneacetonitrile (0.294 mol) were added to a solution of intermediate (1) (0.164 mol) in methanol (200 ml) and the mixture was stirred at room temperature overnight. The mixture was quenched with water and extracted with DCM. The organic layer was dried, filtered off and evaporated till dryness. The residue was recrystallized from DIPE, yielding 47.3 g (70%) of 3-(3-chlorophenyl)-5-[2-(4-chlorophenyl)-1,3-dioxolan-2-yl]-2,1-benzisoxazole (interm. 2).

c) Intermediate (2) (0.0381 mol) in methanol (200 ml) was hydrogenated with Raney nickel (15 g) as a catalyst at room temperature over a 5 hour period under a $3 \times 10^5$ Pa (3 bar) pressure in a Parr apparatus. After uptake of hydrogen, the catalyst was filtered off and the filtrate was evaporated till dryness. The product was used without further purification, yielding 15.7 g of [2-amino-5-[2-(4-chlorophenyl)-1,3-dioxolan-2-yl]-phenyl](3-chlorophenyl)methanone (interm. 3).

d) A mixture of intermediate (3) (0.098 mol) in DCM (400 ml) was stirred at 5–10° C. Trichloroacetyl chloride (0.12 mol) was added dropwise, over a 15-minutes period, at a temperature between 5–10° C. Triethylamine (0.12 mol) was added dropwise, over a 20-minutes period, at 5–10° C. The reaction mixture was stirred for one hour at 5–10° C. Water (250 ml) was added and stirring was continued for 5 minutes. The organic layer was separated, dried, filtered and the solvent was evaporated. The residue was purified over silica gel on a glass filter (eluent: DCM). The desired fractions were collected and the solvent was evaporated. The residue was stirred in ACN, filtered off and dried, yielding 46.5 g (85%) of trichloro-N-[2-(3-chlorophenyl)-4-[2-(4-chlorophenyl)-1,3-dioxolan-2-yl]phenyl]acetamide (interm. 4).

e) A mixture of intermediate (4) (0.078 mol) and ammonium acetate (0.156 mol) in hexamethylphosphorous triamide (HMPT) (300 ml) was stirred for 3 hours at 100° C. The reaction mixture was cooled, poured out into ice water (1500 ml) and precipitation resulted. The precipitate was filtered off, and washed with water. The product was dissolved in DCM. The organic layer was isolated, dried, filtered and the solvent evaporated. The residue was purified three times over silica gel on a glass filter (eluent: $CH_2Cl_2/CH_3OH$ 97/3, then 95/5). The desired fractions were collected and the solvent was evaporated. The residue was stirred in refluxing isopropanol (200 ml). The mixture was cooled and the resulting precipitate was filtered off, washed with DIPE, and dried, yielding 26 g (76%) of 4-(3-chlorophenyl)-6-[2-(4-chlorophenyl)-1,3-dioxolan-2yl]-2(1H)-quinazolinone (interm. 5, mp. 219.5° C.).

f) A mixture of intermediate (5) (0.052 mol) in hydrochloric acid, 3N (250 ml) and methanol (250 ml) was stirred and refluxed for 2 hours. The reaction mixture was cooled. Water (250 ml) was added and the resulting precipitate was filtered off, washed with water, isopropanol and DIPE, then dried, yielding 19.4 g (94.4%) of 6-(4-chlorobenzoyl)-4-(3-chlorophenyl)-2(1H)-quinazolinone (interm. 6; mp. 256.4° C.).

g) A mixture of intermediate (6) (0.005 mol) in methanol (50 ml) was stirred and cooled on an ice-bath (5–10° C.). Sodium borohydride (0.007 mol) was added portionwise over a 15-minutes period (first, dissolution resulted; after 15 minutes precipitation started). The mixture was stirred for 1 hour at room temperature. The mixture was acidified with 1 N HCl. The precipitate was filtered off, washed with DIPE, then dried, yielding 1.6 g (80%) of (±)-4-(3-chlorophenyl)-6-[(4-chlorophenyl)hydroxymethyl]-3,4-dihydro-2(1H)-quinazolinone (interm. 7; mp. 231.4° C.).

h) A mixture of intermediate (7) (0.013 mol) in DCM (60 ml) was stirred at room temperature. Thionyl chloride (0.065 mol) was added dropwise over a 15-minutes period. The reaction mixture was stirred for 3 hours at room temperature. Dissolution resulted. The solvent was evaporated. Toluene was added and azeotroped on the rotary evaporator, yielding 5.4 g of (±)-6-[chloro(4-chlorophenyl)methyl]-4-(3-chlorophenyl)-3,4-dihydro-2(1H)-quinazolinone (interm. 8).

Example A.2 a) A mixture of intermediate (5) (0.0455 mol) in DMF (500 ml) was stirred at room temperature, under $N_2$ flow. A dispersion of sodium hydride (50%) in mineral oil (0.0455 mol) was added portionwise. The reaction mixture was stirred until gas evolution stopped. Iodomethane (0.0455 mol) was added dropwise and the resulting reaction mixture was stirred for 14 hours at room temperature. The solvent was evaporated. Toulene was added and azeotroped on the rotary evaporator. The crude oil was stirred in DCM (300 ml), washed with water (2×250 ml), dried, filtered and the solvent was evaporated. The residue was purified by column chromatography over silica gel (eluent: DCM). The desired fractions were collected and the solvent was evaporated, yielding 16.7 g (80%) of 4-(3-chlorophenyl)-6-[2-(4-chlorophenyl)-1,3-dioxolan-2-yl]-1-methyl-2(1H)-quinazolinone (interm. 9).

b) A mixture of intermediate (9) (0.037 mol) in methanol (300 ml) was stirred at room temperature. Hydrochloric acid (0.75 mol) was added dropwise and the resulting reaction mixture was stirred and refluxed for one hour, then cooled to room temperature and extracted with DCM (2×250 ml). The separated organic layer dried, filtered and the solvent was evaporated. The residue was triturated in PIPE. The precipitate was filtered off, washed with DIPE (100 ml) and dried (vacuum, 60° C.; 14 hours), yielding 12.6 g (83%) of 6-(4-chlorobenzoyl)-4-(3-chlorophenyl)-1-methyl-2(1H)-quinazolinone (interm. 10).

Example A.3 a) A suspension of intermediate (10) (0.031 mol) in methanol (150 ml) was stirred at room temperature. Sodium borohydride (0.062 mol) was added portionwise (maximal temperature rise of 5° C.). The reaction mixture was stirred for 2 hours at room temperature. The precipitate was filtered off, washed with water (50 ml), isopropanol (100 ml) and DIPE (100 ml), then dried (vacuum; 50° C.), yielding 11.5 g (90%) of (±)-4-(3-chlorophenyl)-6-[(4-chlorophenyl)hydroxymethyl]-3,4-dihydro-1-methyl-2(1H)-quinazolinone (interm. 11)

b) DCM (0.0556 mol) was added dropwise to a mixture of intermediate (11) (0.028 mol) in DCM (100 ml). The reaction mixture was stirred and refluxed for 2 hours. The solvent was evaporated. Toulene was added and azeotroped on the rotary evaporator, yielding 12.09 g of (±)-6-[chloro(4-chlorophenyl)methyl]-4-(3-chlorophenyl)-3,4-dihydro-1-methyl-2(1H)-quinazolinone (interm. 12).

Example A.4 a) A solution of intermediate (9) (0.0122 mol) in methanol (50 ml) was cooled to 5° C. Sodium borohydride (0.0122 mol) was added portionwise and the mixture was allowed to stand at 5° C. for 30 minutes. The mixture was poured out on ice-water. The precipitate was filtered off, washed with water and dried, yielding 5.4 g (98%) of (±)-4-(3-chlorophenyl)-6-[2-(4-chlorophenyl)-1,3-dioxolan-2-yl]-3,4-dihydro-1-methyl-2(1H)-quinazolinone (interm. 13).

b) Intermediate (13) (0.0107 mol) was dissolved in DMF (50 ml) at 0° C. under $N_2$ flow. A dispersion of sodium hydride (80%) in mineral oil (0.013 mol) was added and the mixture was allowed to stand at 0° C. for 30 minutes. Iodomethane (0.0215 mol) was added dropwise and the mixture was allowed to stand at 0° C. for 1 hour. The mixture was poured out on ice-water. The precipitate was filtered off, washed with water and taken up in DCM. The organic layer was dried, filtered and the solvent was evaporated, yielding 6.2 g of (±)-4-(3-chlorophenyl)-6-[2-(4-chlorophenyl)-1,3-dioxolan-2-yl]-3,4-dihydro-1,3-dimethyl-2(1H)-quinazolinone (interm. 14).

c) A mixture of intermediate (14) (0.0259 mol) in acetic acid (75 ml), water (20 ml) and THF (10 ml) was stirred and refluxed overnight, and the solvent was evaporated. The residue was taken up in DCM and washed with $K_2CO_3$ (10%). The organic layer was decanted, dried, filtered, and the solvent was evaporated, yielding 11 g (100%) of product. A sample was crystallized from 2-propanone/DIPE. The precipitate was filtered off and dried, yielding 1.5 g of (±)-6-(4-chlorobenzoyl)-4-(3-chlorophenyl)-3,4-dihydro-1,3-dimethyl-2(1H)-quinazolinone (interm. 15).

Example A.5 a) A mixture of intermediate (5) (0.0175 mol) in DMF (80 ml) was cooled on an ice bath under nitrogen flow. Sodium hydride (80% in oil, 0.0228 mol) was added portionwise and the mixture was stirred at a low temperature for 30 minutes, then at room temperature for 1 hour. The mixture was cooled to 5° C. and chloromethyl ethyl ether (0.0228 mol) was added. The mixture was stirred at a low temperature for 30 minutes and then hydrolized. The precipitate was filtered off, washed with water, taken up in DCM, dried, filtered, and the solvent was evaporated till dryness. The residue was purified by column chromatography over silica gel (eluent: $CH_2Cl_2$/$CH_3OH$/$NH_4OH$ 99/1/0.1), yielding 2.9 g (33.3%) of 4-(3-chlorophenyl)-6-[2-(4-chlorophenyl)-1,3-dioxolan-2-yl]-1-(ethoxymethyl)-2(1H)-quinazolinone (interm. 16).

b) A mixture of intermediate (16) (0.0058 mol) in methanol (50 ml) was cooled on an ice bath. Sodium borohydride (0.0058 mol) was added portionwise. The mixture was stirred at a low temperature for 30 minutes, then poured out into ice water and extracted with DCM. The organic layer was separated, dried, filtered, and the solvent was evaporated till dryness, yielding 2.9 g (100%) of (±)-4-(3-chlorophenyl)-6-[2-(4-chlorophenyl)-1,3-dioxolan-2-yl]-1-(ethoxymethyl)-3,4-dihydro-2(1H)-quinazolinone (interm. 17).

c) A mixture of intermediate (17) (0.0058 mol) in DMF (30 ml) was cooled on an ice bath under nitrogen flow. Sodium hydride (80% in oil, 0.007 mol) was added and the mixture was stirred at a low temperature for 30 minutes. Methyl iodide (0.007 mol) was added dropwise. The mixture was stirred at a low temperature for 1 hour, then allowed to warm to room temperature, hydrolized and water was added. The precipitate was filtered off, washed with water, taken up in DCM, dried, filtered, and the solvent was evaporated till dryness, yielding 3 g (100%) of (±)-4-(3-chlorophenyl)-6-[2-(4-chlorophenyl)-1,3-dioxolan-2-yl]-1-(ethoxymethyl)-3,4-dihydro-3-methyl-2(1H)-quinazolinone (interm. 18).

d) A mixture of intermediate (18) (0.0058 mol) in HCl (30 ml) and THF (30 ml) was stirred and refluxed overnight, cooled by adding ice, basified with $NH_3$(aq.) and extracted with DCM. The organic layer was separated, dried, filtered and the solvent was evaporated till dryness. The residue was taken up in 2-propanone and DIPE. The precipitate was filtered off, washed and dried, yielding 2.2 g (91.6%) of (±)-6-(4-chlorobenzoyl)-4-(3-chlorophenyl)-3,4-dihydro3-methyl-2(1H)-quinazolinone (interm. 19).

e) Sodium borohydride (0.0053 mol) was added to a mixture of intermediate (19) (0.0053 mol) in methanol (20 ml) and THF (20 ml), previously cooled on an ice bath (5° C.). The mixture was stirred at 5° C. for 30 minutes, poured out into ice water and extracted with DCM. The organic layer was separated, dried, filtered and the solvent was evaporated till dryness, yielding 2.2 g (100%) of (±)-4-(3-chlorophenyl)-6-[(4-chlorophenyl)hydroxymethyl]-3,4-dihydro-3-methyl-2(1H)-quinazolinone (interm. 20).

f) Thionyl chloride (10 ml) was added dropwise to a mixture of intermediate (20) (0.005 mol) in DCM (50 ml), previously cooled on an ice bath (5° C.). The mixture was stirred at room temperature for 1 night. The solvent was evaporated till dryness. The product was used without further purification, yielding quantitatively (±)-6-[chloro(4-chlorophenyl)methyl]-4-(3-chlorophenyl)-3,4-dihydro-3-methyl-2(1H)-quinazolinone (interm. 21).

B. Preparation of the Final Products

Example B.1

A mixture of intermediate (8) (0.013 mol), imidazole (0.039 mol) and potassium carbonate (0.04 mol) in ACN (75 ml) was stirred and refluxed for 3 hours. The solvent was evaporated. The residue was stirred in water and this mixture was extracted with DCM. The separated organic layer was dried, filtered and the solvent evaporated. The residue was purified over silica gel on a glass filter (eluent: $CH_2Cl_2$/$CH_3OH$ 95/5). The desired fractions were collected and the solvent was evaporated. The residue was purified by column chromatography over silica gel (eluent: $CH_2Cl_2$/$CH_3OH$/($CH_3OH$/$NH_3$) 95/2.5/2.5). The pure fractions were collected and the solvent was evaporated. The residue was stirred in diethyl ether (50 ml), filtered off and dried, yielding 2.6 g (44.5%) of (±)-4-(3-chlorophenyl)-6-[(4-chlorophenyl)-1H-imidazol-1-ylmethyl]-3,4-dihydro-2(1H)-quinazolinone (comp. 8); mp. 177.1° C.

Example B.2

A mixture of 1-methylimidazole (0.073 mol) in the THF (110 ml) was cooled to −70° C. under $N_2$ flow. A solution of n-butyllithium in hexane (1.6M) (45.6 ml) was added dropwise. The mixture was stirred at −70° C. for 30 minutes. Chlorotriethylsilane (0.073 mol) was added. The mixture was allowed to warm slowly to room temperature and then cooled to −70° C. A solution of n-butyllithium in hexane (1.6M) (45.6 ml) was added dropwise. The mixture was stirred at −70° C. for 1 hour, then brought to −15° C. and cooled to −70° C. A mixture of intermediate (10) (0.061 mol) in THF (100 ml) was added. The mixture was stirred at −70° C. for 30 minutes, then brought to 0° C., hydrolized, extracted with ethyl acetate and decanted. The organic layer was dried, filtered and the solvent was evaporated till dryness. The residue was purified by column chromatography over silica gel (eluent: $CH_2Cl_2$/$CH_3OH$/$NH_4OH$ 93/7/0.5), yielding 9.5 g of product. The product was recrystallized from 2-propanone/ACN. The precipitate was filtered off, washed with diethyl ether and dried, yielding 2 g of (±)-4-(3-chlorophenyl)-6-[(4-chlorophenyl)hydroxy(1-methyl-1H-imidazol-5-yl)methyl]-1-methyl-2(1H)-quinazolinone monohydrate (comp. 4).

Example B.3

A mixture of compound (8) (0.0045 mol) and manganese (IV) oxide (0.05 mol) in DCM (50 ml) was stirred for 18 hours at room temperature. The mixture was filtered over dicalite. The dicalite was washed with $CH_2Cl_2$/$CH_3OH$ 90/10. The filtrate was evaporated. The residue was purified over silica gel on a glass filter (eluent: $CH_2Cl_2$/$CH_3OH$ 95/5). The desired fractions were collected and the solvent was evaporated. The residue was purified by column chromatography over silica gel (eluent: $CH_2Cl_2$/$CH_3OH$ 95/5) and recrystallized from ACN (25 ml). The precipitate was filtered off, washed with DIPE, and dried, yielding 1 g (50%) of (±)-4-(3-chlorophenyl)-6-[(4-chlorophenyl)-1H-imidazol-1-ylmethyl]-2(1H)-quinazolinone (comp. 1; mp. 255.1° C.).

Example B.4

Sodium borohydride (0.003 mol) was added portionwise at 5° C. to a mixture of compound (4) (0.003 mol) in methanol (30 ml). The mixture was stirred at 5° C. for 30 minutes, then hydrolyzed, extracted with DCM and decanted. The organic layer was dried, filtered and the solvent was evaporated. The residue was purified by column chromatography over silica gel (eluent: $CH_2Cl_2$/$CH_3OH$/$NH_4OH$). The pure fractions were collected and the solvent was evaporated. The residue was crystallized from diethyl ether. The precipitate was filtered off and dried, yielding 1 g (±)-4-(3-chlorophenyl)-6-[(4-chlorophenyl)hydroxy(1-methyl)-1H-imidazol-5-yl)methyl]-3,4-dihydro-1-methyl-2(1H)-quinazolinone (comp. 13).

Example B.5

A dispersion of sodium hydride in mineral oil (60%) (0.0047 mol) was added portionwise to a mixture of compound (9) (0.0043 mol) in DMF (40 ml) under $N_2$ flow. The mixture was stirred for 30 minutes at room temperature. A solution of iodomethane (0.0047 mol) in DMF (10 ml) was added dropwise and the resulting reaction mixture was stirred overnight at room temperature. The reaction mixture was poured out into water (200 ml) and this mixture was extracted with toluene (3×100 ml). The separated organic layer was dried, filtered and the solvent evaporated. The residue was purified by column chromatography over silica gel (eluent: ethyl acetate/CH$_3$OH/(CH$_3$OH/NH$_3$) 90/5/5). The pure fractions were collected and the solvent was evaporated. This fraction was repurified by column chromatorgraphy over silica gel (eluent: CH$_2$Cl$_2$/CH$_3$OH 100/0, upgrading over 20 minutes to 90/10; 125 ml/min). The pure fractions were collected and the solvent was evaporated, yielding 0.370 g (18%) of (±)-4-(3-chlorophenyl)-6-[(4-chlorophenyl)-1H-imidazol-1-ylmethyl]-3,4-dihydro-1,3-dimethyl-2(1H-quinazolinone (comp. 10).

Example B.6

A dispersion of sodium hydride in mineral oil (60%) (0.01122 mol) was added portionwise to a mixture of compound (1) (0.0051 mol) in DMF (25 ml) under N$_2$ flow. The mixture was stirred for 30 minutes at room temperature. A solution of 4-(chloromethyl)pyridine hydrochloride (0.00561 mol) in DMF (5 ml) was added dropwise and the resulting reaction mixture was stirred over the weekend at room temperature. The reaction mixture was poured out into water and this mixture was extracted with toluene. The separated organic layer was dried, filtered and the solvent evaporated. The residue was purified by column chromatography over silica gel (eluent: CH$_2$Cl$_2$/CH$_3$OH/(CH$_3$OH/NH$_3$) 90/5/5). The desired fractions were collected and the solvent was evaporated. This fraction was repurified by high-performance liquid chromatorgraphy over Kromasil RP-18 (100 Å, 10 μm, 5 cm DAC; eluent: (0.5% NH$_4$OAc in H$_2$O)/CH$_3$OH/CH$_3$CN 47/25/28 v/v). The pure fractions were collected and the organic solvent was evaporated. The aqueous residue was extracted with DCM. The separated organic layer was dried, filtered, and the solvent evaporated, yielding 0.900 g (32.8%) of (±)-4-(3-chlorophenyl)-6-[(4-chlorophenyl)-1H-imidazol-1-ylmethyl]-1-(4-pyridinylmethyl)-2(1H-quinazolinone (comp. 3; mp. 61.4° C.).

Example B.7

A mixture of compound (4) (0.0069 mol) in formamide (34 ml) and acetic acid (68 ml) was stirred at 160° C. for 24 hours, then poured out into ice water and alkalised with a concentrated NH$_3$ (aq.) solution. The precipitate was filtered off, washed with water and taken up in DCM. The organic layer was separated, dried, filtered and the solvent was evaporated till dryness. The residue was purified by column chromatography over silica gel (eluent: CH$_2$Cl$_2$/CH$_3$OH/ NH$_4$OH 96/4/0.2). The pure fractions were collected and the solvent was evaporated. The residue was crystallized from 2-propanone/DIPE. The precipitate was filtered off and dried, yielding 0.85 g of (±)-4-(3-chlorophenyl)-6-[(4-chlorophenyl)(1-methyl-1H-imidazol-5-yl)methyl]-3,4-dihydro-1-methyl-2(1H-quinazolinone (comp. 14).

Example B.8

Compound (4) (0.01 mol) was added at a low temperature to thionyl chloride (50 ml). The mixture was stirred at 40° C. for 2 hours. The solvent was evaporated till dryness. The product was used without further purification, yielding 5.46 g of (±)-6-[chloro(4-chlorophenyl)(1-methyl-1H-imidazol-5-yl)methyl]-4-(3-chlorophenyl)-1-methyl-2(1H-quinazolinone monohydrochloride (comp. 6).

Example B.9

Ammonium hydroxide (50 ml) was cooled to 5° C. A solution of compound (6) (0.01 mol) in THF (50 ml) was added. The mixture was stirred at room temperature for 2 hours, then at 60° C. for 30 minutes and cooled. Ethyl acetate was added. The mixture was decanted. The organic layer was dried, filtered and the solvent was evaporated till dryness. The residue was purified by column chromatography over silica gel (eluent: toulene/isopropanol/NH$_4$OH 75/25/2). The pure fractions were collected and the solvent was evaporated. The residue was crystallized from DCM and diethyl ether. The precipitate was filtered off and dried, yielding 1.1 g of (±)-6-[amino(4-chlorophenyl)(1-methyl-1H-imidazol-5-yl)methyl]-4-(3-chlorophenyl)-1-methyl-2 (1H-quinazolinone (comp. 7).

Example B.10 a) A mixture of interm. (21) (0.0146 mol), 2-phenylimidazole (0.0219 mol) and potassium carbonate (0.0438 mol) in ACN (80 ml) was stirred and refluxed for 4 hours. The solvent was evaporated till dryness. The residue was taken up in DCM and water. The organic layer was separated, dried, filtered and the solvent was evaporated till dryness. The product was used without further purification, yielding a mixture of (±)-4-(3-chlorophenyl)-6-[(4-chlorophenyl)(2-phenyl-1H-imidazol-1-yl)methyl]-2-methoxyquinazoline (interm. 22) and (±)-4-(3-chlorophenyl)-6-[(4-chlorophenyl)(2-phenyl-1H-imidazol-4-yl)methyl]-2-methoxyquinazoline (interm. 23).

b) A mixture of intermediates (22) and (23) (0.0146 mol) in HCl (3 N, 100 ml) and THF (100 ml) was stirred and refluxed for 3 hours, then poured out into ice water and extracted with ethyl acetate. The organic layer was separated, dried, filtered and the solvent was evaporated till dryness. The residue was purified by column chromatorgraphy over silica gel (eluent: CH$_2$Cl$_2$/CH$_3$OH/NH$_4$OH 95/5/0.5). Two pure fractions were collected and their solvents were evaporated. The first fraction was crystallized from ACN, 2-propanone and DIPE, yielding 1.2 g (15.8%) of (±)-4-(3-chlorophenyl)-6-[(4-chlorophenyl)(2-phenyl-1H-imidazol-1-yl)methyl]-2(1H-quinazolinone (comp. 19, mp. 170° C.). The second fraction was dissolved in 2-propanone and DIPE and converted into the ethanedioic acid salt (1:1), yielding 0.8 g (8.7%) of (±)-4-(3-chlorophenyl)-6-[(4- chlorophenyl)(2-phenyl-1H-imidazol-4-yl)methyl]-2(1H) quinazolinone ethanedioate(1:1).monohydrate (comp. 20, mp. 197° C.).

Tables F-1 to F-4 list the compounds that were prepared according to one of the above Examples.

TABLE F-1

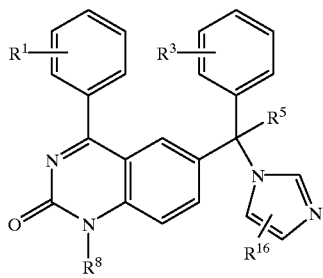

| Co. No. | Ex. No. | $R^1$ | $R^3$ | $R^5$ | $R^8$ | $R^{16}$ | Physical data |
|---|---|---|---|---|---|---|---|
| 1 | B.3 | 3-Cl | 4-Cl | H | H | H | mp. 255.1° C. |
| 2 | B.3 | 3-Cl | 4-Cl | H | CH₃— | H | mp. 123.3° C. |
| 3 | B.6 | 3-Cl | 4-Cl | H | 4-pyridyl-CH₂— | H | mp. 61.4° C. |
| 19 | B.10 | 3-Cl | 4-Cl | H | H | 2-phenyl | mp. 170° C. |

TABLE F-2

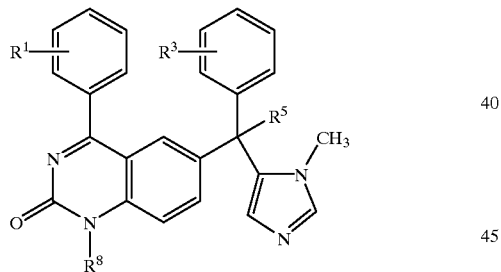

| Co. No. | Ex. No. | $R^1$ | $R^3$ | $R^5$ | $R^8$ | Physical data |
|---|---|---|---|---|---|---|
| 4 | B.2 | 3-Cl | 4-Cl | OH | CH₃ | .H₂O (1:1) |
| 5 | B.3 | 3-Cl | 4-Cl | H | CH₃ | .ethanedioate (1:1).H₂O (1:2) |
| 6 | B.8 | 3-Cl | 4-Cl | Cl | CH₃ | .HCl (1:1) |
| 7 | B.9 | 3-Cl | 4-Cl | NH₂ | CH₃ | — |

TABLE F-3

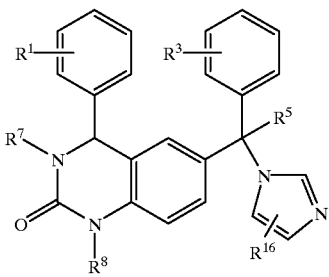

| Co. No. | Ex. No. | R¹ | R³ | R⁵ | R⁷ | R⁸ | R¹⁶ | Physical data |
|---|---|---|---|---|---|---|---|---|
| 8 | B.1 | 3-Cl | 4-Cl | H | H | H | H | mp. 177.1° C. |
| 9 | B.1 | 3-Cl | 4-Cl | H | H | CH₃ | H | mp. 111.5° C. |
| 10 | B.5 | 3-Cl | 4-Cl | H | CH₃ | CH₃ | H | — |
| 11 | B.5 | 3-Cl | 4-Cl | H | CH₂CH₃ | CH₃ | H | mp. 115.8° C. |
| 18 | B.1 | 3-Cl | 4-Cl | H | CH₃ | H | 2-phenyl | mp. 236° C. |

TABLE F-4

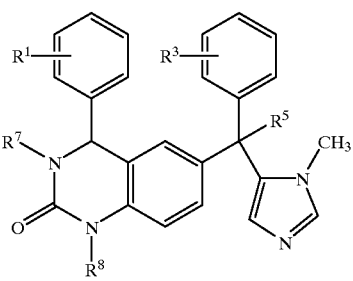

| Co. No. | Ex. No. | R¹ | R³ | R⁵ | R⁷ | R⁸ | Physical data |
|---|---|---|---|---|---|---|---|
| 12 | B.2 | 3-Cl | 4-Cl | OH | CH₃ | CH₃ | — |
| 13 | B.4 | 3-Cl | 4-Cl | OH | H | CH₃ | — |
| 14 | B.7 | 3-Cl | 4-Cl | H | H | CH₃ | — |
| 15 | B.7 | 3-Cl | 4-Cl | H | CH₃ | CH₃ | — |
| 16 | B.8 | 3-Cl | 4-Cl | Cl | CH₃ | CH₃ | .HCl (1:1) |
| 17 | B.9 | 3-Cl | 4-Cl | NH₂ | CH₃ | CH₃ | (A) |

C. Pharmacological Example

Example C.1

"Ras-Transformed Cell Phenotype Reversion Assay"

Insertion of activated oncogenes such as the mutant ras gene into mouse NIH 3T3 cells converts the cells to a transformed phenotype. The cells become tumorigenic, display anchorage independent growth in semi-solid medium and lose contact inhibition. Loss of contact inhibition produces cell cultures which no longer form uniform monolayers. Rather, the cells pile up into multicellular nodules and grow to very high saturation densities in plastic tissue culture dishes. Agents such as protein farnesyl transferase inhibitors which revert the ras transformed phenotype restore the uniform monolayer growth pattern to cells in culture. This reversion is easily monitored by counting the number of cells in tissue culture plates. Transformed cells will achieve higher cell numbers than cells which have reverted to an untransformed phenotype. Compounds which revert the transformed phenotype should produce antitumor effects in tumors bearing ras gene mutations.

Method

Compounds are screened in tissue culture in NIH 3T3 cells transformed by the T24 activated human H-ras gene. Cells are seeded at an initial density of 200,000 cells per well (9.6 cm² surface area) in six-well cluster tissue culture plates. Test compounds are immediately added to 3.0 ml cell growth medium in a 3.0 μl volume of DMSO, with a final concentration of DMSO in the cell growth medium of 0.1%. The test compounds are run at concentrations of 5, 10, 50, 100, and 500 nM along with a DMSO treated vehicle control. (In case a high activity is observed at 5 nM, the test compound is tested at even lower concentrations.) The cells are allowed to proliferate for 72 hours. Then the cells are detached in 1.0 ml trypsin-EDTA cell dissociation medium and counted on a Coulter particle counter.

Measurements

Cell numbers expressed as cells per well are measured using a Coulter Particle Counter. All cell counts were corrected for the initial cell input density by subtracting 200,000. Control cell counts=[cell counts from cells incubated with DMSO vehicle−200,000] Test compound cell counts=[cell counts from cells incubated with test compound−200,000].

$$\text{Test compound \% inhibition} = \left[1 - \frac{\text{test compound cell counts}}{\text{control cell counts}}\right] \times 100\%.$$

Compounds 5, 7, 14 and 15 had an IC$_{50}$ less than 500 nM.

What is claimed is:

1. A compound of formula (I)

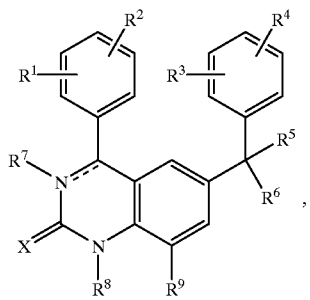

a pharmaceutically acceptable acid addition salt or a stereochemically isomeric form thereof, wherein the dotted line represents an optional bond;

X is oxygen or sulfur;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^1$, $Ar^1C_{1-6}$alkyl, $Ar^1$oxy, $Ar^1C_{1-6}$alkyloxy;

$R^3$ and $R^4$ each independently are hydrogen, halo, cyano, $C_{1-6}$alkyl, $C_{1-6}$alkyloxy, $Ar^1$oxy, $C_{1-6}$alkylthio, di($C_{1-6}$alkyl)amino, trihalomethyl or trihalomethoxy;

$R^5$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, mono- or di($C_{1-6}$alkyl)amino$C_{1-6}$ alkyl, $Ar^1$, $Ar^1C_{1-6}$alkyloxy$C_{1-6}$alkyl; or a radical of formula —O—$R^{10}$, (a-1)

—S—$R^{10}$, (a-2)

—N—$R^{11}R^{12}$, (a-3)

wherein $R^{10}$ is hydrogen, $C_{1-6}$alkyl, $C_{1-6}$alkylcarbonyl, $Ar^1$, $Ar^1C_{1-6}$alkyl, $C_{1-6}$alkyloxycarbonyl$C_{1-6}$alkyl, or a radical of formula —Alk—O$R^{13}$ or —Alk—N$R^{14}R^{15}$;

$R^{11}$ is hydrogen, $C_{1-6}$alkyl, $Ar^1$ or $Ar^1C_{1-6}$alkyl;

$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^1C_{1-6}$alkyl, $C_{1-6}$alkylcarbonyl-$C_{1-6}$alkyl, $Ar^1$carbonyl, $Ar^1C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—O$R^{13}$ or —Alk—N$R^{14}R^{15}$; wherein Alk is $C_{1-6}$alkanediyl;

$R^{13}$ is hydrogen, $C_{1-6}$alkyl, $C_{1-6}$alkylcarbonyl, hydroxy$C_{1-6}$alkyl, $Ar^1$ or $Ar^1C_{1-6}$alkyl;

$R^{14}$ is hydrogen, $C_{1-6}$alkyl, $Ar^1$ or $Ar^1C_{1-6}$alkyl;

$R^{15}$ is hydrogen, $C_{1-6}$alkyl, $C_{1-6}$alkylcarbonyl, $Ar^1$ or $Ar^1C_{1-6}$alkyl;

$R^6$ is a radical of formula

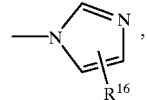
(b-1)

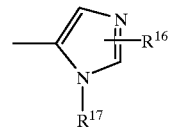
(b-2)

wherein $R^{16}$ is hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2C_{1-6}$alkyl;

$R^{17}$ is hydrogen, $C_{1-6}$alkyl or di($C_{1-4}$alkyl)aminosulfonyl;

$R^7$ is hydrogen or $C_{1-6}$alkyl provided that the dotted line does not represent a bond;

$R^8$ is hydrogen, $C_{1-6}$alkyl or $Ar^2CH_2$ or $Het^1CH_2$;

$R^9$ is hydrogen, $C_{1-6}$alkyl, $C_{1-6}$alkyloxy or halo; or $R^8$ and $R^9$ taken together to form a bivalent radical of formula —CH=CH—, (c-1)

—CH$_2$—CH$_2$—, (c-2)

—CH$_2$—CH$_2$—CH$_2$—, (c-3)

—CH$_2$—O—, or (c-4)

—CH$_2$—CH$_2$—O—; (c-5)

$Ar^1$ is phenyl; or phenyl substituted with 1 or 2 substituents each independently selected from halo, $C_{1-6}$alkyl, $C_{1-6}$alkyloxy or trifluoromethyl;

$Ar^2$ is phenyl; or phenyl substituted with 1 or 2 substituents each independently selected from halo, $C_{1-6}$alkyl, $C_{1-6}$alkyloxy or trifluoromethyl; and $Het^1$ is pyridinyl; pyridinyl substituted with 1 or 2 substituents each independently selected from halo, $C_{1-6}$alkyl, $C_{1-6}$alkyloxy or trifluoromethyl.

2. A compound according to claim 1 wherein $R^1$ and $R^2$ are each independently selected from hydrogen, halo or $C_{1-4}$alkyl, $R^3$ and $R^4$ are each independently selected from hydrogen, halo or $C_{1-4}$alkyl, $R^5$ is hydrogen, hydroxy, halo or a amino; $R^6$ is a radical of formula (b-1) or (b-2) wherein $R^{16}$ is hydrogen or $C_{1-4}$alkyl and $R^{17}$ is $C_{1-4}$alkyl; $R^7$ is hydrogen or $C_{1-4}$alkyl in case the dotted line does not represent a bond; $R^8$ is hydrogen; $C_{1-4}$alkyl or $Het^1CH_2$; and $R^9$ is hydrogen.

3. A compound according to any of claim 1 wherein X is oxygen, $R^1$ is 3-chloro, $R^2$ is hydrogen, $R^3$ is 4-chloro, $R^4$ is hydrogen, $R^5$ is hydrogen, $C_{1-2}$alkyl, halo or amino; $R^6$ is a radical of formula (b-1) or (b-2) wherein $R^{16}$ is hydrogen and $R^{17}$ is $C_{1-2}$alkyl; and $R^7$ is hydrogen or $C_{1-2}$alkyl in case the dotted line does not represent a bond; $R^8$ is hydrogen; $C_{1-2}$alkyl or Het$^1$CH$_2$; and $R^9$ is hydrogen.

4. A compound according to claim 1 wherein the compound is

6-[amino(4-chlorophenyl)(1-methyl-1H-imidazol-5-yl)methyl]-4-(3-chlorophenyl)-1-methyl-2(1H)-quinazolinone; or 6-[amino(4-chlorophenyl)(1-methyl-1H-imidazol-5-yl)methyl]-4-(3-chlorophenyl)-3,4-dihydro-1,3-dimethyl-2(1H)-quinazolinone; a stereoisomeric form or a pharmaceutically acceptable acid addition salt thereof.

5. A pharmaceutical composition comprising a pharmaceutically acceptable carrier, and as active ingredient a therapeutically effective amount of a compound as described of claim 1.

6. A compound of formula (XI)

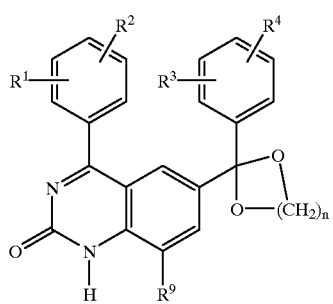

(XI)

an acid addition salt or a stereochemically isomeric form thereof, wherein n is 2 or 3 and $R^1$, $R^2$, $R^3$, $R^4$ and $R^9$ are as defined in claim 1.

7. A process for preparing a compound of formula (I) wherein a) an intermediate of formula (III) is N-alkylated with an intermediate of formula (II) in a reaction-inert solvent and, optionally in the presence of a suitable base, yielding a compound of formula (I-a);

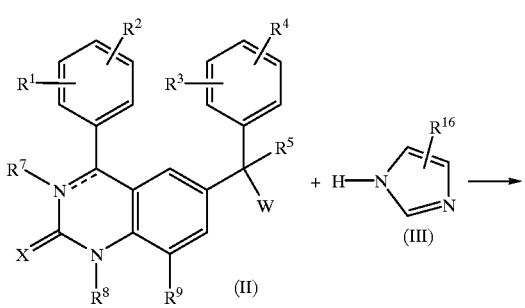

b) an intermediate of formula (IV) is reacted with a compound of formula (V), yielding a compound of formula (I-a);

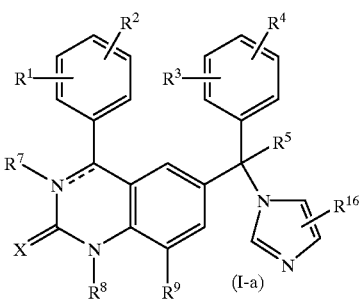

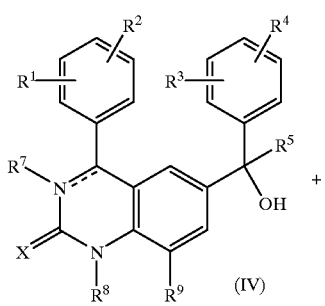

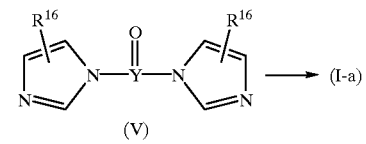

c) an intermediate ketone of formula (VI) is reacted with an intermediate of formula (III-1) or (III-2) in the presence of a suitable strong base and in the presence an appropriate silanederivative, optionally followed by removal of a protective group PG; yielding either a compound of formula (I-b-1) or (I-b-2);

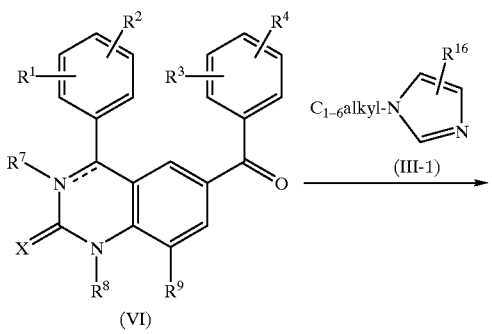

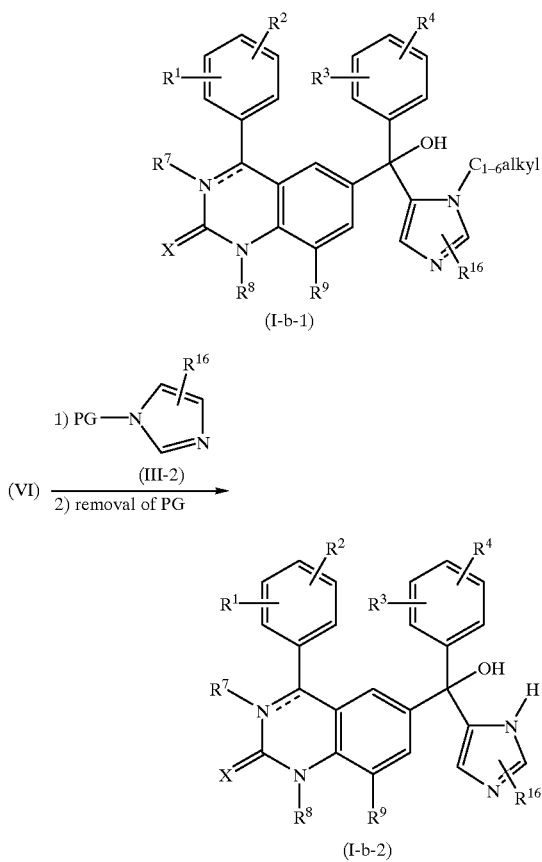

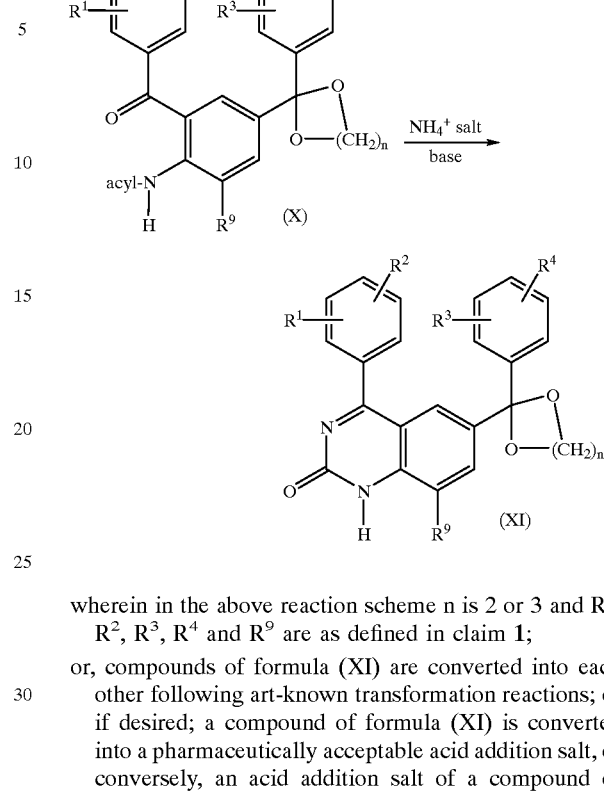

wherein in the above reaction scheme n is 2 or 3 and $R^1$, $R^2$, $R^3$, $R^4$ and $R^9$ are as defined in claim 1;

or, compounds of formula (XI) are converted into each other following art-known transformation reactions; or if desired; a compound of formula (XI) is converted into a pharmaceutically acceptable acid addition salt, or conversely, an acid addition salt of a compound of formula (XI) is converted into a free base form with alkali; and, if desired, preparing stereochemically isomeric forms thereof.

9. A method for inhibiting the abnormal growth of cells in a mammal in need thereof comprising administering an effective amount of a compound as claimed in claim 1.

10. A method for inhibiting tumor growth in a mammal in need thereof comprising administering an effective amount of a compound as claimed in claim 1.

11. A method for inhibiting the growth of tumors expressing an activated ras oncogene in a mammal in need thereof comprising administering a compound as claimed in claim 1.

12. A method for inhibiting proliferative diseases wherein ras proteins are activated as a result of oncogenic mutation in genes in a mammal in need thereof comprising administering a compound as claimed in claim 1.

wherein in the above reaction schemes the dotted line and the radicals X, $R^1$, $R^2$, $R^3$, $R^4$, $R^5$, $R^6$, $R^7$, $R^8$, $R^9$ and $R^{16}$ are as defined in claim 1 and W is an appropriate leaving group;

d) or, compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

8. A process for preparing a compound of formula (XI) as claimed in claim 6 wherein an intermediate of formula (X) is cyclized in the presence of an ammonium salt and an appropriate base;

* * * * *